(12) United States Patent
Mettendorf et al.

(10) Patent No.: US 7,852,983 B2
(45) Date of Patent: Dec. 14, 2010

(54) X-RAY DIFFRACTOMETER FOR MECHANICALLY CORRELATED MOVEMENT OF THE SOURCE, DETECTOR, AND SAMPLE POSITION

(75) Inventors: Kai Uwe Mettendorf, Karlsruhe (DE); Claus Bolzinger, Karlsruhe (DE); Joachim Lange, Hagenbach (DE)

(73) Assignee: Bruker AXS GmbH, Karlsruhe (DE)

( * ) Notice: Subject to any disclaimer, the term of this patent is extended or adjusted under 35 U.S.C. 154(b) by 0 days.

(21) Appl. No.: 12/385,685

(22) Filed: Apr. 16, 2009

(65) Prior Publication Data

US 2009/0262895 A1    Oct. 22, 2009

(30) Foreign Application Priority Data

Apr. 22, 2008    (DE) ........................ 10 2008 020 108

(51) Int. Cl.
*G01N 23/20* (2006.01)

(52) U.S. Cl. ........................................... 378/79; 378/71

(58) Field of Classification Search .................. 378/71, 378/79, 81
See application file for complete search history.

(56) References Cited

U.S. PATENT DOCUMENTS

| | | | |
|---|---|---|---|
| 2,898,469 A | 8/1959 | Rose | |
| 3,073,952 A | 1/1963 | Rose | |
| 4,446,568 A | 5/1984 | Williams | |
| 4,637,041 A * | 1/1987 | Brinkgreve et al. | ........... 378/71 |
| 4,771,446 A | 9/1988 | Howe | |

FOREIGN PATENT DOCUMENTS

| | | |
|---|---|---|
| DE | 101 39 645 | 3/2003 |
| EP | 1 681 561 | 7/2006 |
| JP | 03186743 | 3/1991 |
| JP | 06 066 741 | 3/1994 |
| JP | 06-066741 | 3/1994 |
| JP | 06 313 757 | 11/1994 |
| JP | 11014566 | 1/1999 |
| WO | WO 2005/015187 | 2/2005 |

* cited by examiner

*Primary Examiner*—Chih-Cheng G Kao
(74) *Attorney, Agent, or Firm*—Paul Vincent

(57) ABSTRACT

An X-ray diffractometer has a mechanism without toothed ring and is suited to move the two legs of a goniometer, on which the source and detector are respectively disposed, at the same time and in a correlated fashion. Each goniometer leg (or linkage) thereby has a common main center of rotation HDP and also one respective auxiliary center of rotation HD1, HD2. The two auxiliary centers of rotation are symmetrically disposed with respect to a symmetry plane E which contains the main center of rotation, and can be moved on a guidance that is symmetrical with respect to the plane E. The main center of rotation can only be moved in the plane E, e.g. along a rail guidance. The movement of the main center of rotation relative to the guidance can be easily driven by means of one single motor.

17 Claims, 6 Drawing Sheets

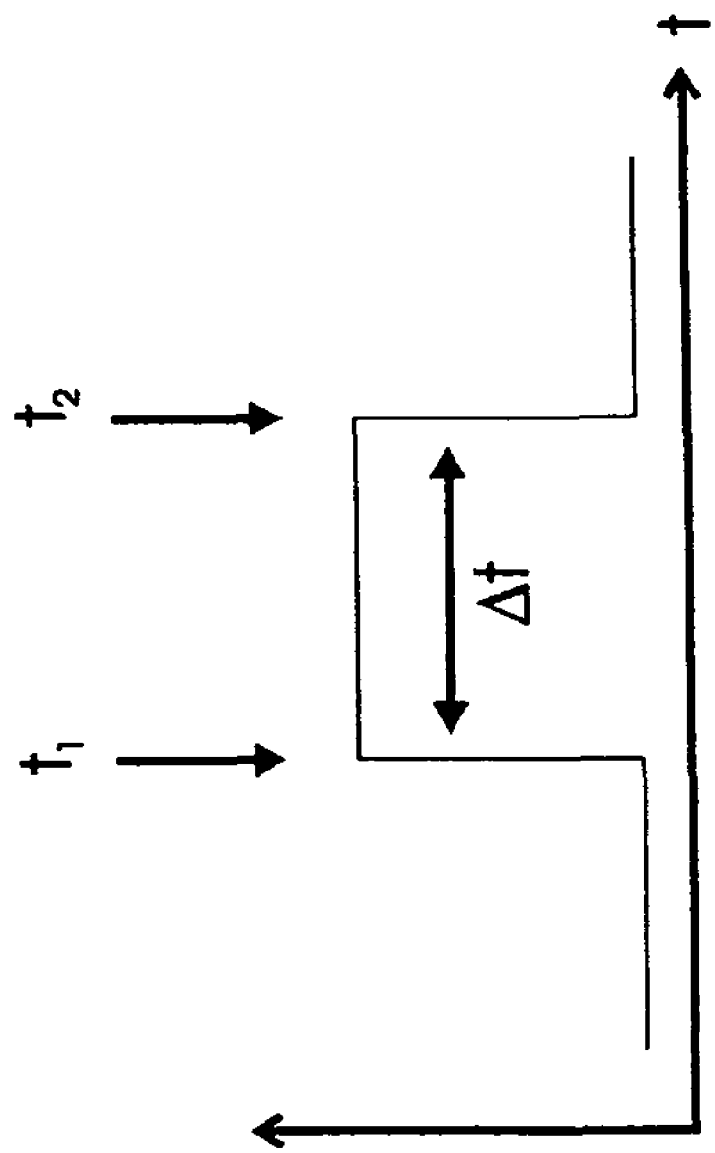

X-RAY DIFFRACTOMETER FOR MECHANICALLY CORRELATED MOVEMENT OF THE SOURCE, DETECTOR, AND SAMPLE POSITION

This application claims Paris Convention priority of DE 10 2008 020 108.1 filed Apr. 22, 2008 the complete disclosure of which is hereby incorporated by reference.

BACKGROUND OF THE INVENTION

The invention concerns a diffractometer, comprising a source for generating X-ray radiation, a sample position for arranging a sample, and a detector for detecting X-ray radiation emitted by the sample, wherein the source and the detector can be rotated with respect to an axis A that extends through the sample position, and wherein the source, the sample position, and the detector are disposed in a common plane M that extends perpendicularly to the axis A.

A diffractometer of this type is disclosed e.g. by the document JP6066741.

X-ray diffractometry is used in a plurality of ways in order to analyze crystalline (and to a certain degree also amorphous) components of samples. X-ray radiation is thereby diffracted on crystal planes in the sample. The spatial intensity distribution of the diffracted X-ray radiation, in particular the position of intensity maxima ("reflexes") can e.g. give information about the interlattice plane distance and thereby about the crystal lattice (lattice symmetry) or also about preferred lattice plane orientations (textures). The basic connection between the interlattice plane distance, the angle of incidence and the wavelength of X-ray radiation is described by Bragg's law.

In X-ray diffraction experiments, the normal to the observed lattice plane group forms the bisector of the incident and emergent X-rays. An overall X-ray measurement for determining an X-ray data set consists of many individual measurements of integral intensities with different beam geometries. During one overall X-ray measurement, which comprises many integrals of individual measurements, the X-ray source and/or the X-ray detector are correspondingly moved and/or the sample is tilted.

In some measuring methods, in particular, when tilting of the sample shall be prevented during an X-ray measurement, both the source and the detector must be moved around the sample on respective circular arcs during the overall X-ray measurement (measurement of one data set).

An X-ray diffractometer with a source that can be moved on a first circular arc and a detector that can be moved on a second circular arc is disclosed in JP6066741. In conventional devices, the source and the detector are normally each driven by their own motor, and the movements are synchronized through electronic control of the two motors in accordance with the requirements of the measuring method, generally in a Θ-Θ-geometry or Θ-2Θ-geometry. In another conventional method, the source as well as the detector are moved via two separate transmissions by only one motor.

In both cases, the diffractometer construction is quite complex and therefore expensive.

It is the underlying purpose of the invention to present a diffractometer having a greatly simplified construction, in which the source and the detector can be moved on circular arcs in accordance with a Θ-Θ-geometry.

SUMMARY OF THE INVENTION

This object is achieved by a diffractometer of the above-mentioned type, which is characterized in that a first linkage is provided, which is disposed such that it can be rotated about the axis A, and to which the source is mounted, a second linkage is provided, which is also disposed such that it can be rotated about the axis A, and to which the detector is mounted, the first linkage is moreover disposed on a first auxiliary center of rotation HD1 such that it can be rotated about a first auxiliary axis HA1, wherein the first auxiliary axis HA1 extends parallel to the axis A and has a fixed separation AB therefrom, the second linkage is disposed on a second auxiliary center of rotation HD2 such that it can be rotated about a second auxiliary axis HA2, wherein the second auxiliary axis HA2 also extends parallel to the axis A and also has a fixed separation AB therefrom, a guidance is provided along which one or both auxiliary centers of rotation HD1, HD2 can be moved, wherein the guidance extends mirror-symmetrically with respect to a plane E that contains the axis A and has the same separation from the two auxiliary centers of rotation HD1, HD2, wherein the sample position can be moved relative to the guidance in an x direction, wherein the x direction extends in the plane E and perpendicularly to the axis A.

The inventive diffractometer has a substantially triangular basic construction. Centers of rotation are disposed at the corners of this triangle, i.e. the two auxiliary centers of rotation HD1 and HD2 and also a main center of rotation HDP at the location of the axis A. The two linkages ("legs") connect the main center of rotation HDP to the auxiliary centers of rotation with respectively fixed and identical separation AB. The guidance correlates the two auxiliary centers of rotation HD1, HD2 with respect to the symmetry plane E. The two linkages are opened and closed like a pair of scissors when the sample position is moved (relative to the guidance). In the simplest case, both auxiliary centers of rotation can be moved on the guidance. When the sample position, and thereby the main center of rotation HDP, are moved relative to the guidance along the plane E, the linkages force relative tracking of the auxiliary centers of rotation HD1, HD2 along the guidance. Since the guidance extends symmetrically with respect to the plane E, and the separations AB are fixed and identical, the positions thereby always change in the same fashion, in particular the separations of the auxiliary centers of rotation HD1 and HD2 with respect to the plane E. This ensures that the two linkages are always pivoted by the same angle but in opposite directions about the main center of rotation HDP or the axis A. Since the source and the detector are disposed on the linkages, a Θ-Θ-condition for the X-ray radiation with respect to the sample position on the main center of rotation HDP can always be maintained.

The relative motion of the sample position and the guidance ("x movement") through which an overall X-ray measurement can be run through in a Θ range of approximately 0°-80° in a Bragg-Brentano measurement geometry, can be driven by one single simple translation motor. In particular, the sample position can thereby be moved with stationary guidance by a motor along a stationary rail that extends in the plane E. The auxiliary centers of rotation may also be moved by a motor on a stationary guidance (e.g. with a threaded rod) and the sample position also slides e.g. along a rail. It is also possible to keep the sample position at a stationary point and move the guidance by a motor in the x direction, wherein the auxiliary centers of rotation can additionally slide on the guidance. When the sample position is stationary, the auxiliary centers of rotation may also be moved by a motor on the guidance, wherein the guidance can slide in the x direction, e.g. in a stationary rail. In any case, passage of a desired Θ area is very simple; the Θ-Θ-condition is always automatically kept by the diffractometer mechanics.

When the sample position is stationary, the guidance is moved in the x direction and when the guidance is stationary, the sample position is moved in the x direction (the absolute movement of sample position and guidance is not important for an angular scan). The simplest construction of the inventive diffractometer is generally realized by a stationary guidance, on which both auxiliary centers of rotation (driven or not driven) can be moved. If only one auxiliary center of rotation can be moved with respect to the guidance, the sample position can be moved (in addition to the x movement) in correspondence with the direction of guidance of the guidance in order to provide a degree of freedom. In this case, the guidance should simply extend in a straight line. It must be noted that an axial machine component is typically formed at the location of the (mathematical) axis A, on which the linkage is disposed.

In the inventive diffractometer, the X-ray source and the X-ray detector can be pivoted and the (relative) position of the sample can be adjusted by means of only one drive. This omits, in particular, any expensive toothed rings in the transmissions for coordination or selection of the different movements. The costs are considerably reduced, since the inventive diffractometer needs only one drive (preferably and typically one linear drive), and no complex transmission mechanism is required. The inventive diffractometer can therefore be designed, in particular, as an inexpensive tabletop device. The inventive diffractometer can be used to perform X-ray measurements in the Bragg-Brentano measuring geometry.

In a preferred embodiment of the inventive diffractometer, the separation QP between the source and the sample position is equal to the separation PD between the sample position and the detector. The detector position is thereby typically defined by the position of the detector collimator. In the Bragg-Brentano geometry, the divergent X-ray radiation that is emitted by the source is approximately refocused by the flat sample to the detector. The flat sample thereby tangentially abuts the focussing circle that is given by the points of source position, detector collimator position and main center of rotation HDP at the sample position.

In an advantageous embodiment, the guidance extends in a straight line. This is easy to realize, in particular, in view of the guidance of the auxiliary centers of rotation that can be moved.

In a preferred embodiment, both auxiliary centers of rotation HD1, HD2 can be moved in opposite directions on the guidance. This construction can be realized in a particularly simple fashion, e.g. by means of two carriages on a continuous rail or two carriages on two separate (and typically coaxial) rail sections. For this reason, one can do without the otherwise required degrees of freedom of guidance or sample position with respect to translation, the mechanical realization of which is complex. In another preferred embodiment, the linkages are designed in each case such that the sample position, the associated auxiliary center of rotation HD1, HD2 and the source or the detector form one triangle each, in particular an equilateral triangle, in the plane M. This embodiment achieves a favorable force distribution in the linkages (with little tendency to jam) and in the bearings (e.g. of the sample position and the auxiliary centers of rotation) over a large Θ angular range. The respective auxiliary center of rotation forms the peak on the respective linkage. The linkages can be designed, in particular, in a V-shape. A V-shape that is open to the top has proven to be particularly suitable (FIG. 2).

One particularly preferred embodiment has a motor drive for moving the sample position relative to the guidance. The motor drive can act on the sample position and/or on one or both auxiliary centers of rotation and/or the guidance. The drive preferably comprises an electronic control for exact control of the relative position of the sample position and guidance as a function of time, such that a sequence of integral individual measurements of an overall X-ray measurement can be easily automated.

In an advantageous further development of this embodiment, the guidance is stationary and the sample position can be moved along a stationary rail by means of the motor drive. This, in turn, simplifies construction of the diffractometer. The sample position is typically defined via a sample holder (or a sample receptacle) that is moved. The guidance is generally not moved (not translated). Stationary in this case means that the location does not change within the scope of the angular scan of an overall X-ray measurement (wherein a possible superposed movement of the diffractometer as a whole is neglected).

In another preferred further development, the guidance comprises a threaded rod which is driven by the motor drive. At least one auxiliary center of rotation and preferably both auxiliary centers of rotation are seated in an engaging fashion on the threaded rod and are linearly moved thereon through its rotation. In this fashion, a rotary motion that is typical for a motor can be very easily converted into a translation, in the present case of the auxiliary point(s) of rotation.

In a particularly preferred further development, a control means is provided for the motor drive, which advances the sample position in the x direction in accordance with a predetermined time function x(t), in particular, such that the detector sweeps the same angular increments within the same time. The control means provides automated measuring operation, and thereby, in particular, defined positioning of the source and the detector as a function of time t. When the detector is to sweep the same angular increments within the same time, x(t) is selected in a non-linear fashion such that $d/dt\ \Theta(t)=$const. It must be noted that x(t) can thereby be changed continuously or in discrete steps. The control function x(t) is thereby determined from the connection $\Theta(x)$ that results from the diffractometer geometry, with x: position of the sample position relative to the guidance; and Θ: angle of incidence of the X-ray radiation, by means of $d/dt\ [\Theta(x)]=d\Theta/dx*dx/dt=$const. If the relation $d/dt\ \Theta(t)=$const. applies, an intensity profile $I(\Theta)$ ("diffractogram") can be directly produced from intensities that are measured at different angle positions and are integrated over respectively identical times Δt. It must be noted that the x-position of the sample position must basically be regarded as being relative to the guidance.

Another preferred further development is characterized in that a control means is provided for the motor drive, which advances the sample position in the x direction in accordance with a predetermined time function x(t) with $d/dt\ x(t)=$const. and that an evaluation means is provided which takes into consideration a non-linear connection $\Theta(x)$ in determining an intensity profile $I(\Theta)$ of the sample. If necessary, the evaluation means can control the detector, e.g. clock the individual measurements (i.e. variable integration time Δt). In general, the motor drive can be easily controlled with a constant speed of x (or a linear connection between x and t) in terms of mechanical and control technology (in particular, in a much simpler and less expensive fashion than a non-linear connection between x and t). An evaluation via software that is not adjusted to a non-constant d/dt Θ(t) can be realized at minimum cost. Detailed information about possible modes of operation of the evaluation means is given below. It must be noted again that the x position of the sample position is basically to be regarded relative to the guidance.

In a further development, the control means corrects an intensity $I(t_i)$ determined within a time interval $t_i$ through multiplication by a factor $$\left.\frac{d\vartheta}{dx}\right|_{xi},$$

with i: index of the integral individual measurements and $x_i$: average x-value for individual measurement i.

In a particularly preferred embodiment of the inventive diffractometer, the detector is designed as a one-dimensional detector with an elongated detector window, wherein the detector window extends in the plane M over its entire length. In the one-dimensional detector, several detector elements are arranged one behind the other on the detector. All detector elements are thereby positioned in the (measuring) plane M. The one-dimensional detector can considerably increase the overall number of simultaneously registered X-ray pulses, which improves the signal-to-noise-ratio. Particular details in connection with the evaluation of measurements with the one-dimensional detector are explained below. The one-dimensional detector is an alternative to the zero-dimensional detector that is used as the simplest case in connection with the invention.

In another particularly preferred embodiment, the diffractometer is designed in such a fashion that a sample that is disposed at the sample position maintains its orientation during relative motion of the sample position and the guidance, in particular, wherein the sample that is disposed at the sample position is oriented in a horizontal or perpendicular fashion. This embodiment also particularly facilitates handling (in the horizontal orientation) of samples that are sensitive to tilting, in particular liquid samples. In the simplest case, the sample holder or the sample position is fixed (no translation, no tilting) or only the sample position or the sample holder is moved during the relative motion (translation, but not tilting). In practice, the latter is usually the case, wherein the sample holder including sample or sample position is only moved in a vertical direction. However, a sample can be rotated about a vertical axis during an individual or overall measurement, e.g. for averaging. The vertical sample orientation is particularly advantageous for measurements in transmission geometry.

Further advantages of the invention can be extracted from the description and the drawing. The features mentioned above and below may be used in accordance with the invention individually or collectively in arbitrary combination. The embodiments shown and described are not to be understood as an exhaustive enumeration but have exemplary character for describing the invention.

The invention is illustrated in the drawing and explained in more detail with reference to embodiments.

BRIEF DESCRIPTION OF THE DRAWING

FIG. 6 shows an illustration of a measuring interval for an individual X-ray measurement with an inventive diffractometer.

DESCRIPTION OF THE PREFERRED EMBODIMENT

I. Inventive Diffractometers

Figure 1:
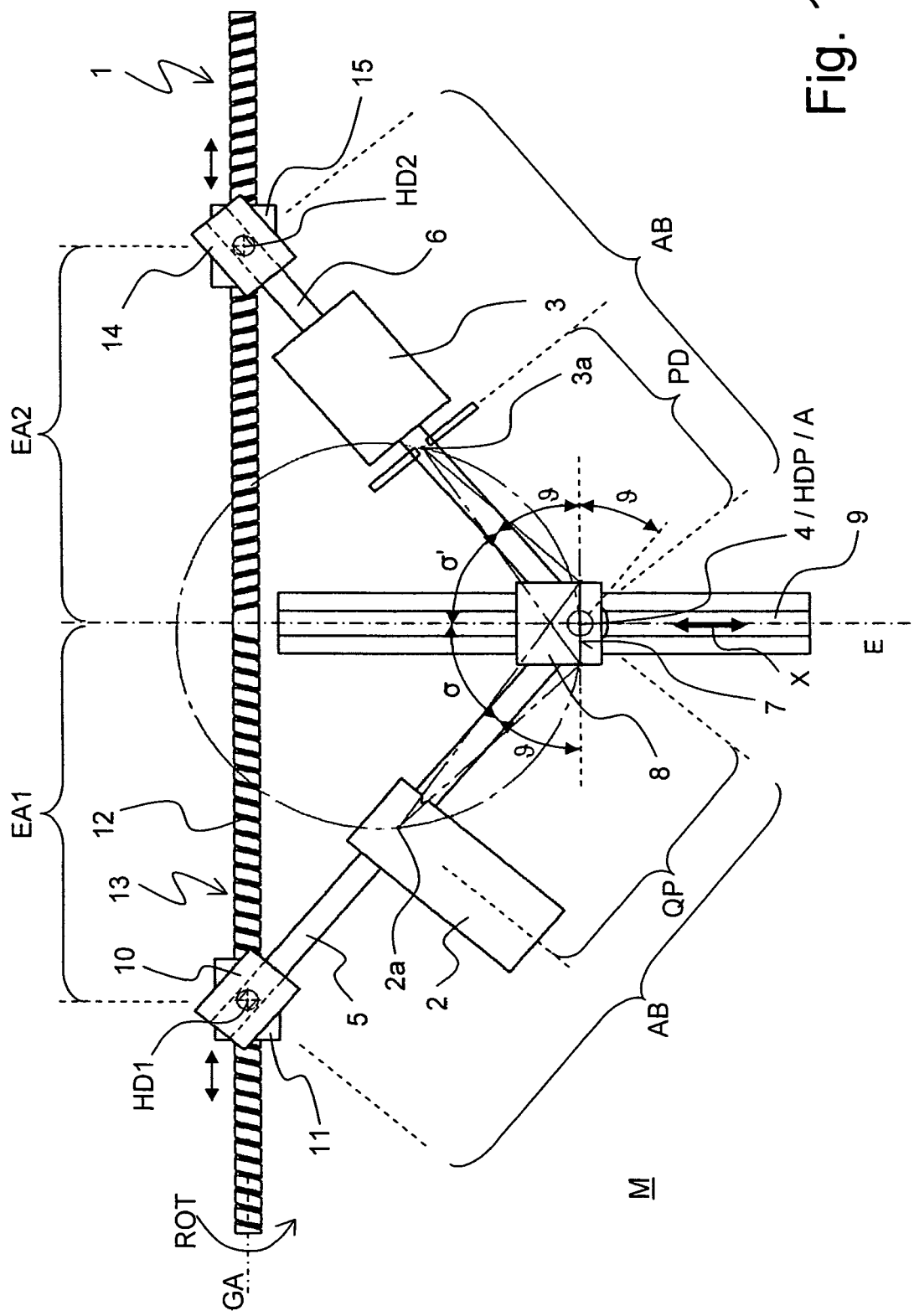
FIG. 1 shows a schematic side view of a first embodiment of an inventive diffractometer in a so-called "V geometry"

FIG. 1 shows a first embodiment of an inventive diffractometer 1, comprising a source 2 for X-ray radiation, in the present case an X-ray tube, a detector 3, in the present case a zero-dimensional detector with only one registering element for X-ray radiation, and a sample position 4 for arrangement of a sample (in the present case with a flat sample holder 7; the center of the sample holder 7 is associated with the sample position 4). The sample holder 7 is disposed on a carriage 8 that can freely slide in a vertical stationary rail 9.

The source 2 is rigidly mounted to a first linkage 5 that is disposed to be rotatable about an axis A (that extends perpendicularly to the plane of the drawing). The axis A thereby extends through the sample position 4. The detector 3 is rigidly mounted to a second linkage 6 that is also disposed to be rotatable about the axis A. The point of intersection of the linkages at the location of the axis A is thereby associated with a common main center of rotation HDP of the two linkages 5, 6. When the carriage 8 is moved in a vertical direction along the rail 9, the sample position and the main center of rotation HDP also move.

The first linkage 5 terminates at its end facing away from the sample position 4 in an end piece 10 that is rotatably disposed on a counter piece 11 of a straight threaded rod 12 (see the associated first auxiliary center of rotation HD1). The counter piece 11 has an inner thread that engages in the outer thread of the threaded rod 12. When the threaded rod rotates (see arrow ROT) about the axis of the threaded rod GA, the counter piece 11 moves along the threaded rod 12 in a horizontal direction. In this respect, the threaded rod 12 acts as a guidance 13: When the counter piece 11 moves along the threaded rod axis GA, the first auxiliary center of rotation HD1 as well as the end piece also move.

One further end piece 14 is analogously formed on the second linkage 6, which is disposed on a further counter piece 15 of the threaded rod 12 such that it can be rotated about the second auxiliary center of rotation HD2. It must be noted that the direction of rotation of the outer thread changes in the center of the threaded rod 12, such that the movements of the counter piece 11 and the further counter piece 15 are opposite to each other when the threaded rod 12 rotates.

It must be noted that the respective axes of rotation of the main center of rotation HDP, the first auxiliary center of rotation HD1 and the second auxiliary center of rotation HD2 are oriented parallel with respect to each other.

The threaded rod 12 can be driven by a motor in a manner that is not shown in detail. In the presented embodiment, the threaded rod 12 is held stationary (but at the same time rotatable for rotation ROT) in bearings that are not shown in detail.

The linkage 5, 6 and the guidance 13 (i.e. the threaded rod 12) are designed mirror-symmetrically with respect to a plane E. The main center of rotation HDP is in the plane E. The separations EA1 and EA2 of the first center of rotation HD1 and the second center of rotation HD2 from the plane E are equal. The angle σ, at which the source 2 irradiates X-ray radiation onto the sample position (in the present case measured with respect to the plane E), and the angle σ', at which the detector registers the sample position 4 X-ray radiation (in the present case again measured with respect to the plane E) are also equal. The direction of extension of the guidance 13 is mirror-symmetrical on both sides of the plane E (it must be noted that symmetry is not required outside of the range of movement of the complementary pieces 11, 15).

The separations AB between the first auxiliary center of rotation HD1 and the main center of rotation HDP and between the second center of rotation HD2 and the main center of rotation HDP are equal (and fixed, namely predetermined by the length of the linkages 5, 6). The separation QP between the source 2 and the sample position 4 (the location of the source 2 is thereby drawn in the figure at the location of the X-ray anode 2a), and the separation PD between the sample position 4 and the detector 3 (the location of the detector is drawn in the figure at the location of a detector collimator 3a) are also fixed, namely predetermined by the respective mounting positions on the linkages 5, 6. The separations QP and PD are preferably equal. In this case, a beam divergence of the X-ray radiation in case of reflection on the sample is refocused at the sample position 4. It must be noted that the sample position 4, the source location in the drawing (X-ray anode 2a in the present case) and the detector location in the drawing (detector collimator 3a in the present case) are located in a common plane M (the plane of the drawing).

In response to rotation ROT of the threaded rod 12 in a first direction of rotation, the two counter pieces 11, 15 move on the guidance 13 towards the inside, i.e. towards the plane E. EA1=EA2 applies at all times, although the amounts of EA1 and EA2 decrease. Since the two separations AB remain fixed, the carriage 8, and thereby also the sample position 4, are moved downwardly on the rail 9. The direction of movement of the sample position 4 on the rail 9 relative to the guidance 13 is characterized in FIG. 1 as the x-direction (the x-direction extends perpendicularly to the connecting line of the two auxiliary centers of rotation HD1, HD2 and perpendicularly to the axis A). During movement, the angles σ and σ' decrease, wherein σ=σ' always applies. The sample holder 7 thereby always remains horizontal.

When the threaded rod 12 rotates in the other direction, the counter pieces 11, 15 move towards the outside and the sample position 4 moves upwardly.

Due to the position of the X-direction in the symmetry plane E, the fixed and identical separations AB, and the mirror symmetry of the guidance 13 with respect to the plane E, the angular symmetry σ=σ' is maintained during each relative movement of the sample position 4 in the x-direction. It is thereby not important whether the motor drive acts on the auxiliary centers of rotation HD1, HD2 (or the counter pieces 11, 15) or on the sample position 4 (or the carriage 9). The complementary angles for 90° of σ and σ' are the angles of incidence and emergence Θ of the X-ray radiation, which also maintain the same values. For this reason, a Θ-Θ-geometry is kept in all positions of movement. This is achieved in accordance with the invention by the goniometer mechanism of the linkages 5, 6 of the guidance 13, of the main center of rotation HDP and the auxiliary centers of rotation HD1, HD2. The plane E remains stationary in the illustrated embodiment.

It must be noted that for the goniometer mechanism according to FIG. 1, one of the counter pieces 11, 15 may also be designed as a carriage that freely slides on the guidance 13. A driven counter piece (that engages in the threaded rod 12) is sufficient in order to force the relative movement of the sample position 4 in the x direction. This movement also acts, via the associated linkage, on the carriage that freely slides on the guidance.

Due to the V-like shape of the linkages 5, 6, the geometry of the diffractometer structure of FIG. 1 is also called "V goniometer".

It must also be noted that in a more complex inventive diffractometer construction, one of the auxiliary centers of rotation may also be stationary (and not movable along the guidance 13). In this case, the main center of rotation HDP (or the sample position 4) must be movable not only perpendicularly to the guidance 13 but also with a component parallel to the guidance 13 (the sample position 4 must be able to rotate about the stationary auxiliary center of rotation by means of the associated linkage). This means that the plane E is also displaced during the relative motion of the sample position and the guidance, i.e. in a horizontal direction.

Figure 2:
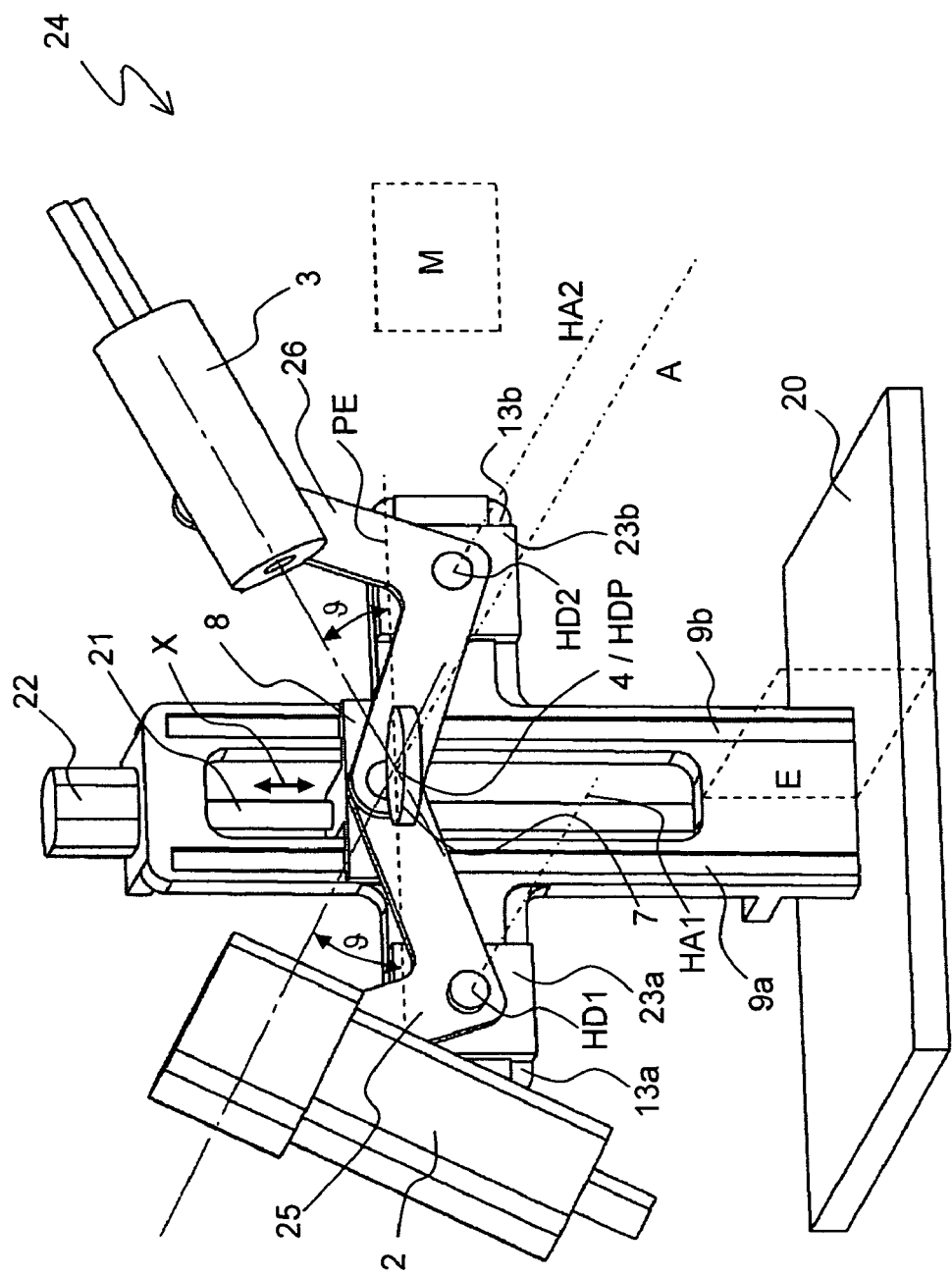
FIG. 2 shows a schematic inclined view of a second embodiment of an inventive diffractometer in a so-called "Y geometry"

FIG. 2 shows a further embodiment of an inventive diffractometer 24. It comprises a basic frame 20 in which a vertical threaded rod 21 is disposed such that it can be rotated. The threaded rod 21 can be driven via a motor 22. Two stationary rails 9a, 9b are moreover formed on the basic frame 20, in which a carriage 8 can be moved. The carriage 8 is at the same time the counter piece of the threaded rod 21 and thereby movable in an x-direction along the rails 9a, 9b by the motor 22.

A stationary two-piece guidance 13a, 13b is moreover formed on the basic frame 20 through horizontal rails. A freely displaceable carriage 23a, 23b is disposed on each partial section 13a, 13b of the guidance. One auxiliary center of rotation HD1, HD2 is formed on each carriage 23a, 23b, around which an associated linkage 25, 26 is disposed that is rotatable with respect to an auxiliary axis HA1, HA2. The first linkage 25 and the second linkage 26 are thereby approximately V-shaped. The partial sections 13a, 13b of the guidance extend in a straight line in a horizontal direction and coaxially with respect to each other.

Both linkages 25, 26 are moreover rotatably disposed on a main center of rotation HDP, which is formed on the carriage 8. The associated axis (of rotation) A extends in a horizontal direction through the main center of rotation HDP. The axis of rotation A extends further through a sample position 4 that is defined by a flat sample holder 7 (or its center). The sample holder 7 is mounted to the carriage 8 and can be moved with it.

A source 2 for X-ray radiation is mounted to the outer end of the first linkage 25. It directs an X-ray at an angle of incidence Θ onto the sample position 4. A detector 3 is mounted to the outer end of the second linkage 26. It registers X-ray radiation that also emerges from the sample position 4 at an angle of emergence of Θ. (angles of incidence and emergence are measured with respect to the sample plane PE that is horizontal in the present case and is defined by the sample holder 7).

The two auxiliary centers of rotation HD1, HD2 are mirror-symmetrical with respect to each other relative to a plane E which is oriented in a vertical direction and contains the axis A (the plane E thereby "divides" the diffractometer 24 in the center).

The sample position 4 can be moved along the x-direction in the plane E by means of the motor 22 and the threaded rod 21. Movement of the sample position 4 or the carriage 8 in the rails 9a, 9b causes rotation of the linkages 25, 26 about the respective auxiliary centers of rotation HD1, HD2 and moreover movement of the auxiliary centers of rotation HD1, HD2 (or the carriages 23a, 23b) on the two-piece guidance 13a, 13b. This also causes simultaneous coordinated movement of the positions of the source 2 and of the detector 3. The latter is associated with an identical change of the angles of incidence and emergence Θ on the sample position 4. An extended Θ angular range can thereby be swept with only one motor 22 (a translation motor for the carriage 8) for one overall X-ray measurement. Due to the Y-like shape of the basic frame 20, in particular of the two-piece guidance 13a, 13b and the rails 9a, 9b, the geometry of the diffractometer construction of FIG. 2 is also called "Y goniometer".

Figure 3:
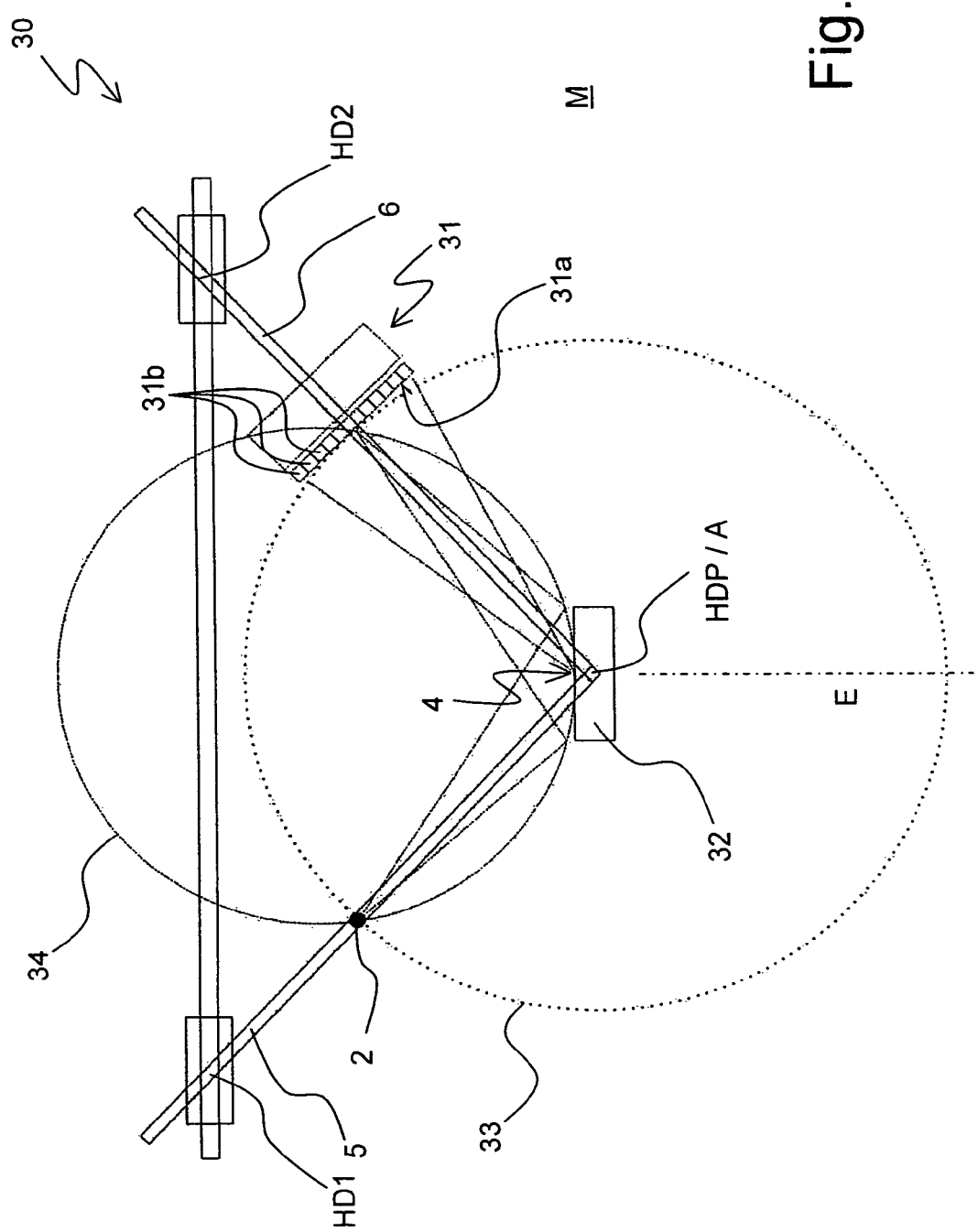
FIG. 3 shows a third embodiment of an inventive diffractometer in "V geometry" with a one-dimensional detector.

FIG. 3 schematically shows the construction of an embodiment of an inventive X-ray diffractometer 30 similar to the embodiment of FIG. 1 with a one-dimensional detector 31.

The linkages 5, 6 are rotatably disposed about the main center of rotation HDP or the axis A. The source 2 is disposed on the first linkage, such that it can be moved on a circular arc 33 about the main center of rotation HDP. The detector 31 is disposed on the second linkage 6 at the same separation from the main center of rotation HDP, such that it can also be moved on the circular arc 33 about the main center of rotation. The circular arc 33 is called the measuring circle.

A focussing circle 34 is additionally illustrated, which is described by the source 2, the sample position 4 (or the sample holder 32) and the center of a detector window 31a of the detector 31. The detector window 31a has a plurality of detector elements 31b, which are lined up in a straight line over the length of the detector window 31a (note that the length of the elongated detector window 31a in FIG. 3 is exaggerated). In the present case, the detector window 31a tangentially abuts the circular arc 33.

Figure 4:
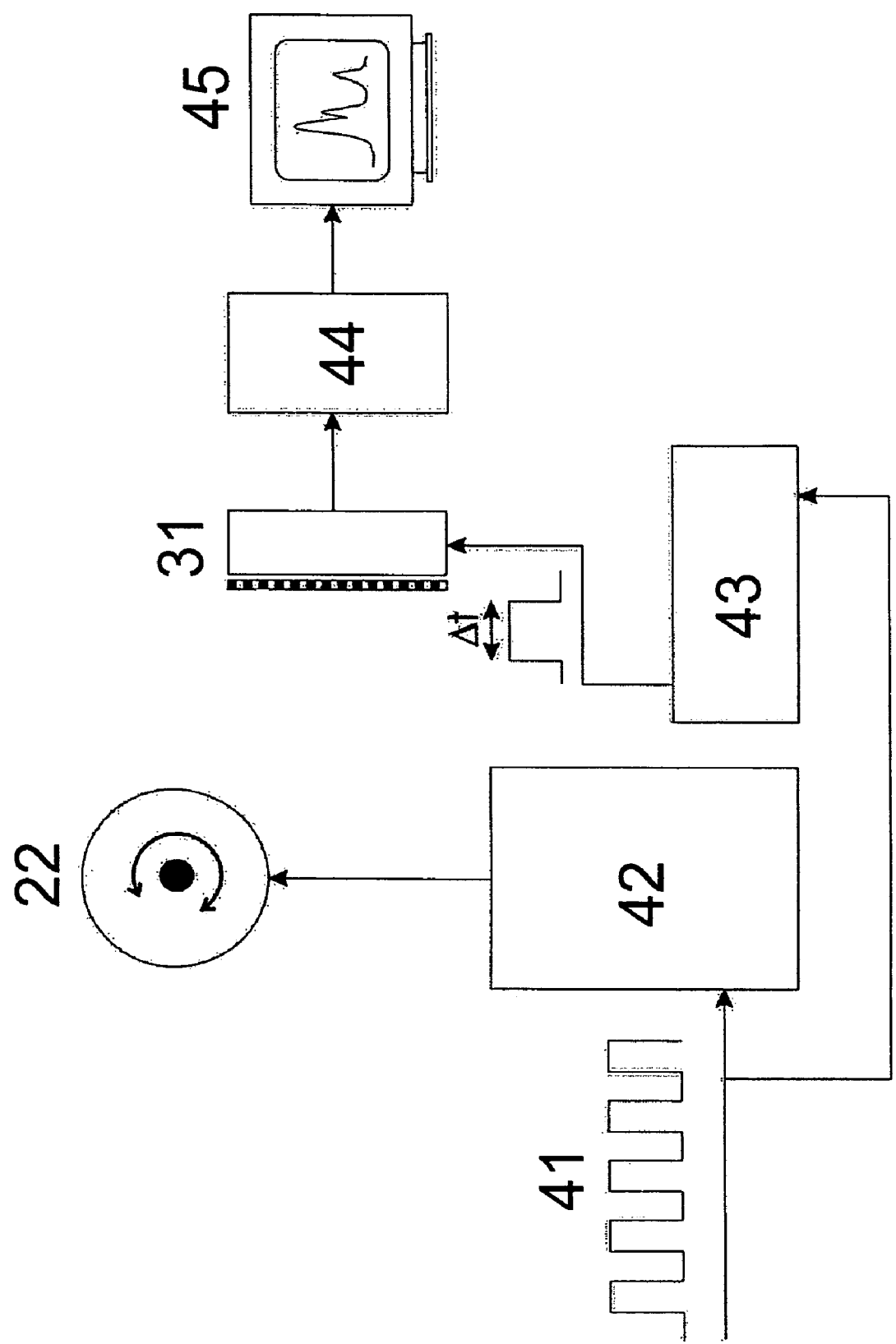
FIG. 4 shows a schematic view of a motor drive unit with detector evaluation for an inventive diffractometer.

FIG. 4 shows the connection of an inventive diffractometer, in particular, of the diffractometer of FIG. 3, to an electronic motor control and detector evaluation.

A periodic control signal 41 is entered into a control means 42 for the motor drive (motor) and a detector control 43. The control means 42 drives the motor 22 (the motor 22 can e.g. be coupled to a threaded rod), wherein a predetermined course x(t) is typically maintained (X:position of the sample position relative to the guidance; t: time).

The detector control 43 extracts a drive control for the detector 31 from the control signal 41 (typically in coordination with the motor control 42). In particular, the integration times Δt of the channels of the detector 31 can be predetermined as a function of the x-position of the sample position. The signals registered by the detector 31 are read out by an evaluation unit 44, are processed (optionally thereby using correction functions) and passed to a computer 45 in the form of an intensity profile I(Θ). Note that the detector control 43 and the evaluation unit 44 may be formed in a combined device.

II. Example for the Mathematical Description of the Geometry of an Inventive Diffractometer X-ray measuring methods, which can be operated with an inventive diffractometer, are described below.

In order to be able to perform an overall X-ray measurement, which comprises a plurality of individual measurements at different Θ-positions, it must be possible to assume different Θ-positions in a defined fashion. The motor drive generally controls the x position of the sample position relative to the guidance, wherein the guidance is generally stationary and the sample position is moved (in particular in FIG. 2). A Θ-position (Θ: angles of incidence and emergence of the X-ray radiation at the sample in the sample position) can be derived from the x position when the mechanical construction of the inventive diffractometer is known. This is explicitly done in the present case for the geometry of a diffractometer in accordance with FIG. 2 ("Y goniometer"). The derivative d Θ(x)/dx can then also be determined from the geometrical function Θ(x), which is required in many cases for the evaluation of detector measuring results (see IV).

Figure 5A:
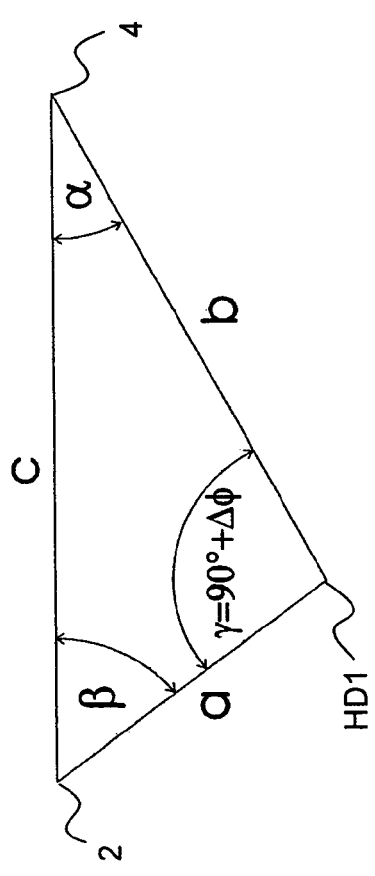
FIG. 5a shows a schematic view of the geometric relationships on an inventive diffractometer similar to FIG. 2 at Θ=0°.
Figure 5B:
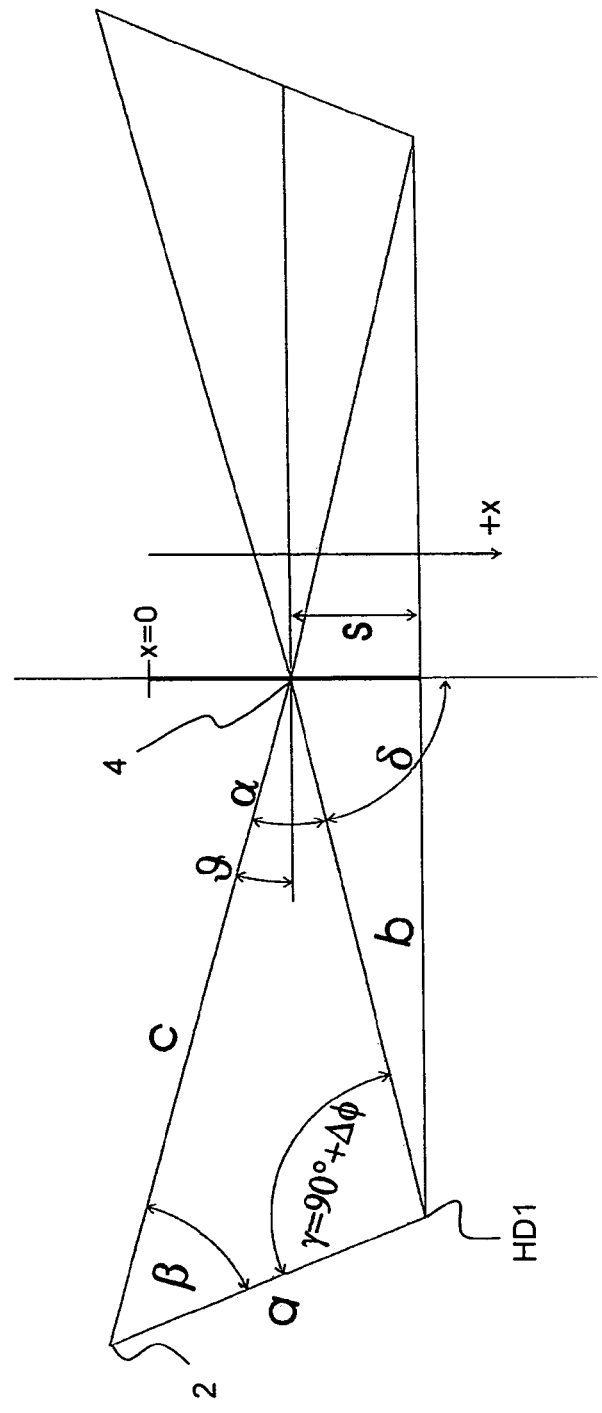
FIG. 5b shows a schematic view of the geometric relationships on an inventive diffractometer similar to FIG. 2 at Θ>0°.

The location of the source 2 in the drawing, the first auxiliary center of rotation HD1, and the sample position 4 form a triangle with side lengths a, b, c and inner angles α, β, and γ (see FIG. 5a and FIG. 5b). FIG. 5b also defines the auxiliary coordinate s and the auxiliary angle δ.

It is assumed that the angle on the first auxiliary center of rotation HD1 has a small deviation Δφ from 90°.

The sample position 4 can be moved in the x direction (vertically). Horizontal irradiation (Θ=0) of the sample position 4 by the source 2 is assumed to be the zero point for the x position (FIG. 5a). The functional relationship between x and Θ can then be determined as follows:

1) a) $s = (b \sin \alpha - x)$
   b) $s = b \cos \delta$
   c) $b \sin \alpha - x = b \cos \delta$ d) $\delta = \arccos\left(\frac{b\sin\alpha - x}{b}\right)$ 2) a) $\Theta = \delta + \alpha - 90°$ b) $\vartheta(x) = \arccos\left(\frac{b\sin\alpha - x}{b}\right) + \alpha - 90°$ 3) in the event of a "non ideal triangle":
   a) $a \neq b$
   b) $\gamma \neq 90° \rightarrow \gamma = 90° + \Delta\phi$
   c) triangle equation:
      $c^2 = a^2 + b^2 - 2ab \cos(90° + \Delta\phi) =$
      $= a^2 + b^2 - 2ab(\cos 90° \cos \Delta\phi - \sin 90° \sin \Delta\phi)$
      $\cos 90° = 0$
      $\sin 90° = 1$
      $\sin \Delta\phi \approx \Delta\phi$ for small $\Delta\phi$
      $\rightarrow c^2 \approx a^2 + b^2 + 2ab\Delta\phi$
   d) triangle equation:
      $a^2 = b^2 + c^2 - 2bc \cos \alpha \rightarrow c^2 = a^2 - b^2 + 2bc \cos \alpha$
   e) $\rightarrow c^2 = a^2 - b^2 + 2bc \cos \alpha \approx a^2 + b^2 + 2ab\Delta\phi$
      $\rightarrow b + 2a\Delta\phi = -b + 2c \cos \alpha$ $\cos \alpha = \frac{b + a\Delta\phi}{c} \rightarrow \alpha = \arccos\left(\frac{b + a\Delta\phi}{c}\right)$ 4) $a = \arccos\left(\frac{b + a\Delta\phi}{\sqrt{a^2 + b^2 + 2ab\Delta\phi}}\right)$ 5a) $\vartheta(x) = \arccos\left(\frac{b\sin\left(\arccos\left(\frac{b + a\Delta\phi}{\sqrt{a^2 + b^2 + 2ab\Delta\phi}}\right)\right) - x}{b}\right) +$
    $\arccos\left(\frac{b + a\Delta\phi}{\sqrt{a^2 + b^2 + 2ab\Delta\phi}}\right) - 90°$ 5b) This formula 5a) can be easily solved for x to obtain x(Θ). The above-mentioned formula x(Θ) can be differentiated according to the normal mathematical rules to obtain dx/dΘ.

6) special case (equilateral triangle with y=90°) Δϕ=0; a=b:

$$\vartheta(x) = \arccos\left(\frac{b\sin\left(\arccos\left(\frac{b}{\sqrt{a^2+b^2}}\right)\right)-x}{b}\right) + \arccos\left(\frac{b}{\sqrt{a^2+b^2}}\right) - 90°$$

$$\vartheta(x) = \arccos\left(\frac{b\sin\left(\arccos\left(\frac{1}{\sqrt{2}}\right)\right)-x}{b}\right) + \arccos\left(\frac{1}{\sqrt{2}}\right) - 90°$$

$$\vartheta(x) = \arccos\left(\frac{b\sin(45°)-x}{b}\right) + 45° - 90°$$

$$\vartheta(x) = \arccos\left(\frac{\sqrt{\frac{b^2}{2}}-x}{b}\right) - 45° = \arccos\left(\frac{\sqrt{\frac{b^2}{2}}-x}{b}\right) - \frac{\pi}{4}$$

7) Derivative of Θ(x) (formula 6 for a=b and Δϕ=0) for x:

$$\frac{\partial \vartheta(x)}{\partial x} = \frac{1}{b\sqrt{1-\frac{\left(\sqrt{\frac{b^2}{2}}-x\right)^2}{b^2}}}$$

III. Detection of Measured Values with Conventional X-ray Diffraction Diffractometers (Goniometers)

Measurements in the step-scan mode (SSM):

For "intensity measurements" with X-ray diffractometers, the integral intensity I(h) is proportional to the square of the absolute value of the structural factor F(h) (h: reciprocal lattice vector). A I(Θ) diagram is thereby measured in [$\Theta_i = \Theta_{min} \ldots \Theta_{max}$] with n equidistant ΔΘ-steps and constant measuring time Δt:

$$I(\underline{h}) = \int_{\vartheta_{min}}^{\vartheta_{max}} I(\vartheta)d\vartheta \propto |F(\underline{h})|^2 \tag{1a}$$

$$I(\underline{h}) \approx \Delta\vartheta \sum_i I(\vartheta_i) \tag{1b}$$

Measurements in the continuous-scan mode (CSM):

This timesaving mode utilizes angular speeds dΘ/dt=const. with simultaneous measurement. While sweeping small areas ΔΘ=const. (see above), counting pulses are "collected" in Δt and associated with the center of ΔΘ. The result is a I(Θ)-diagram. Since in this case, the angular speed is used, the measuring range can be divided into time intervals Δt instead of ΔΘ. For dΘ/dt=const. both points of view are equivalent (ΔΘ and Δt remain constant during the measurement).

$$I(\underline{h}) = \int_{\vartheta_{min}}^{\vartheta_{max}} I(\vartheta)d\vartheta \tag{2}$$

$$= \int_{t(\vartheta_{min})}^{t(\vartheta_{max})} I(\vartheta(t))\frac{d\vartheta}{dt}dt$$

$$= \frac{d\vartheta}{dt}\int_{t(\vartheta_{min})}^{t(\vartheta_{max})} I(t)dt \propto \int_{t(\vartheta_{min})}^{t(\vartheta_{max})} I(t)dt$$

$$\approx \Delta t \sum_i I(t_i)$$

IV. Detection of Measured Values with the Inventive X-ray Diffraction Diffractometers Geometry of the Y goniometer:

For geometrical considerations, the formulas (3), (4), (5) and (6) are found for the inventive Y goniometer (assumption: equilateral geometry with side length b and 90° angle, see also II.). For the coordinate of the linear movement, the following applies: for x=0→Θ(x=0)=0. Formulas for non-equilateral geometry and angles≠90° are considerably more comprehensive (see II.).

$$\vartheta(x) = \arccos\left(\frac{1}{\sqrt{2}} - \frac{x}{b}\right) - \frac{\pi}{4} \tag{3}$$

$$\frac{\partial \vartheta(x)}{\partial x} = \left(b\sqrt{1-\left(\frac{1}{\sqrt{2}} - \frac{x}{b}\right)^2}\right)^{-1} \tag{4}$$

$$x(\vartheta) = \sqrt{\frac{b^2}{2}} - b\cos\left(\vartheta + \frac{\pi}{4}\right) \tag{5}$$

$$\frac{dx(\vartheta)}{d\vartheta} = b\sin\left(\vartheta + \frac{\pi}{4}\right) \tag{6}$$

Measurements with 0d detector

1) SSM mode: Δx such that ΔΘ=const. and Δt=const. The length Δx is calculated from (6) according to (7), by which the motor must be moved in order to keep ΔΘ constant. Subsequently Δt is measured. The resulting I(Θ)-diagram is evaluated in accordance with (1b).

$$\Delta x(\vartheta) = \frac{dx(\vartheta)}{d\vartheta}\Delta\vartheta = \frac{dx(\vartheta)}{d\vartheta} \cdot const \tag{7}$$

2) SSM mode: Δx=const. and Δt=const. Detector and X-ray source move at ΔΘ≠const., such that dΘ integration is not possible. One obtains an I(x)-diagram with Δx=const. I(x) can be integrated over x using ΔΘ=dΘ/dx·Δx to obtain I(h). Any measured value I(Θ($x_i$))=I($x_i$) is thereby multiplied by the "correction factor" dΘ/dx at point $x_i$ (=dΘ/dx|$_{xi}$) and then integrated or added up over x.

$$\int_{\vartheta_{min}}^{\vartheta_{max}} I(\vartheta)d\vartheta = \int_{x(\vartheta_{min})}^{x(\vartheta_{max})} I(\vartheta(x))\frac{d\vartheta}{dx}dx \tag{8}$$

$$\approx \Delta x \sum_i I(x_i)\frac{d\vartheta(x)}{dx}\bigg|_{x_i}$$

3) CSM mode with dx/dt adjustment. If permitted by the control electronics, the motor speed dx/dt can be varied during movement such that dΘ/dt=const. It is now possible to repeatedly recalculate the speed dx/dt|$_{\Theta i}$ through (9) at position $\Theta_i = \Theta_{start} + i \cdot \Delta\Theta_v$ (i=0 . . . n) each time in small steps $\Delta\Theta_v$ and to readjust the motor speed. Since dΘ/dt=const. remains, one can continue as described in (2), since a normal I(Θ) diagram will be obtained.

$$\frac{dx}{dt} = \frac{dx}{d\vartheta}\frac{d\vartheta}{dt} = \frac{dx}{d\vartheta}\dot{\vartheta} \tag{9}$$

4) CSM mode without dx/dt adjustment: If the control electronics only allows dx/dt=const., dΘ/dt≠const. and counting rate corrections are required, since the detector sweeps changing angular intervals ΔΘ with constant measuring times Δt. One practically multiplies each I value measured in the time interval [$t_i,t_i+\Delta t$] and at the position ($x_i,\Theta_i$) by dΘ/dx|$_{xi}$ and sums over all values.

$$\int_{\vartheta_{min}}^{\vartheta_{max}} I(\vartheta)d\vartheta = \int_{t(\vartheta_{min})}^{t(\vartheta_{max})} I(\vartheta(t))\frac{d\vartheta}{dt}dt \tag{10}$$

$$= \int_{t(\vartheta_{min})}^{t(\vartheta_{max})} I(t)\frac{d\vartheta}{dx}\frac{dx}{dt}dt$$

$$= \int_{t(\vartheta_{min})}^{t(\vartheta_{max})} I(t)\frac{d\vartheta}{dt}\dot{x}dt$$

$$\approx \Delta t\dot{x}\sum_{i} I(t_i)\frac{d\vartheta}{dx}\bigg|_i$$

Measurements with 1d Detector with m Linearly and Equidistantly Arranged Measuring Elements (Detector Elements)

1) CSM mode with dx/dt adjustment: The method is the same as above (9). This is the simplest solution provided dx/dt can be changed during the time of movement.
2) CSM mode without dx/dt adjustment: In this case, dx/dt=const. and therefore dΘ/dt≠const. The detector must be properly triggered at any time (see FIG. 6: Measuring time triggering starts at flank $t_1$ and read out after the measuring time Δt at $t_2$). The detected angular range of the detector elements $p_i$ is $\Delta\Theta_p$, that of the entire detector is [$\Theta_{start},\Theta_{start}+(m-1)\Delta\Theta_p$]. Each $p_i$ can be associated with one value $\Theta_j$ at a time $t_k$. When the detector moves by $+\Delta\Theta_p$, the measured value of $p_{i-1}$ must be associated with (added to) the value $\Theta_j$ of the previous $p_i$. This is realized via a storage medium, the registers $R_j$ of which are associated with the angular values $\Theta_j$. During movement, the measured values of the elements $p_i$ are added to the register contents. These allocations must be correctly performed for all m elements through the entire measuring range and at all times. If not, the resulting I(Θ) diagram is useless, showing shifted and clearly "smeared" reflexes. At dx/dt=const., the detector requires different $\Delta t_i$ in dependence on the instantaneous value $\Theta_{start}$ for sweeping $\Delta\Theta_p$. At a constant speed dx/dt, (11) applies. The area ΔΘ that is swept during the measuring time $\Delta t_i$ shall be constant $\Delta\Theta_p$ and is calculated at a position under consideration ($\Theta_{i,xi}$) according to (12).

$$\frac{dx}{dt} = const. = \dot{x} = \frac{dx}{d\vartheta}\frac{d\vartheta}{dt} \rightarrow \frac{d\vartheta}{dt} = \frac{\dot{x}}{\frac{dx(\vartheta)}{d\vartheta}} \text{ or} \tag{11}$$

$$\frac{d\vartheta}{dt} = \frac{d\vartheta}{dx}\frac{dx}{dt} = \frac{d\vartheta}{dx}\dot{x}$$

-continued $$\Delta\vartheta_p = \frac{d\vartheta}{dt}\bigg|_{\vartheta_i(x_i)}\Delta t_i \tag{12}$$

$$= \frac{d\vartheta}{dx}\bigg|_{x_i}\frac{dx}{dt}\Delta t_i$$

$$= \frac{d\vartheta}{dx}\bigg|_{x_i}\dot{x}\Delta t_i \rightarrow \Delta t_i$$

$$= \left(\frac{d\vartheta}{dx}\bigg|_{x_i}\dot{x}\right)^{-1}\Delta\vartheta_p$$

Practical realization: The electronics controls $x_i$ of the linear drive and thereby $\Theta_i$ of the detector. At a position under consideration ($\Theta_i,x_i$), dΘ/dx is calculated, and the required measuring time $\Delta t_i$ for the detector is calculated through (12). In the i-th measurement, the detector sweeps the same $\Delta\Theta_p$ with $\Delta t_i$ and the elements $p_i$ can be unambiguously allocated to the angular values. One obtains a diagram $I_t(\Theta)$, wherein both "shifting" and "smearing" of the reflexes is prevented. The overall correction exceeds the above-described timely start and measurement of the detector, since the $\Delta t_i$ are different. For this reason, a counting pulse correction $\Phi(\Theta_i)$ is required. Excessively high counting pulse values $I_t(\Theta_i)$ must then be divided by the larger value of dx/dΘ. It must thereby be noted that each of the m detector elements contributes to the same value $\Theta_i$ at different positions $\Theta_{start}$ and speeds. The counting pulse correction $\Phi(\Theta)$ is therefore a convolution of the detector window function $w(\Theta)$ (width $\Theta=m\Delta\Theta_p$) and dx(Θ)/dΘ with $w(\Theta)=0$ for $\Theta<-\Theta/2$, $w(\Theta)=1$ for $-\Theta/2\leq\Theta\leq\Theta/2$ and $w(\Theta)=0$ for $\Theta>\Theta/2$.

$$\Phi(\vartheta') = \frac{dx(\vartheta)}{d\vartheta} * w(\vartheta) \tag{13}$$

$$= \int_{-\infty}^{+\infty} \frac{dx(\vartheta)}{d\vartheta}w(\vartheta'-\vartheta)d\vartheta$$

$$= \int_{\vartheta=\vartheta'-\frac{\Theta}{2}}^{\vartheta=\vartheta'+\frac{\Theta}{2}} \frac{dx(\vartheta)}{d\vartheta}d\vartheta$$

$$\Phi(\vartheta) = b\left(\cos\left(\vartheta - \frac{w}{2} + \frac{\pi}{4}\right) - \cos\left(\vartheta + \frac{w}{2} + \frac{\pi}{4}\right)\right) \tag{14}$$

When all m detector elements have passed the position $\Theta_i$ during the scan and their counting pulses have been added up in the storage medium $R_i$, this value $I_t(\Theta_i)$ must be corrected with $\Phi(\Theta_i)$ according to (15).

$$I(\vartheta_i) = \frac{I_t(\vartheta_i)}{\Phi(\vartheta_i)} \tag{15}$$

In summary, the present invention describes an X-ray diffractometer with a mechanism without toothed ring, which is suited to move the two legs of a goniometer, on which the source and detector are respectively disposed, at the same time and in a correlated fashion, wherein the Θ-angle can be scanned, and at the same time a Θ-Θ-geometry (Bragg-Brentano measurement geometry) is always kept. This is achieved in that the goniometer legs (or linkages) each have a common main center of rotation and also one respective auxiliary center of rotation. The two auxiliary centers of rotation are symmetrically disposed with respect to a symmetry plane E that contains the main center of rotation, and can be moved on a guidance that is symmetrical with respect to the plane E. The main center of rotation can only be moved in the plane E, e.g.

along a rail guidance. When the main center of rotation, on which the sample to be measured is arranged, is moved in the plane E, the guidance and the goniometer legs cause an opposite angular shift of the goniometer legs, such that the Θ-Θ-geometry with respect to source and detector is maintained. The movement of the main center of rotation relative to the guidance can be easily driven by means of one single motor.

We claim:

1. A diffractometer comprising:
   a source for generating X-ray radiation;
   means defining a sample position for disposition of a sample;
   a detector for registration of X-ray radiation emitted by the sample, wherein said source and said detector can be rotated with respect to an axis A that extends through said sample position, said source, said sample position and said detector being disposed in a common plane M that is perpendicular to said axis A;
   a first linkage disposed for rotation about said axis A and to which said source is mounted, said first linkage disposed at a first auxiliary center for rotation about a first auxiliary axis extending parallel to said axis A and at a fixed first separation therefrom;
   a second linkage disposed for rotation about said axis A and to which said detector is mounted, said second linkage disposed on a second auxiliary center for rotation about a second auxiliary axis extending parallel to said axis A at said fixed first separation therefrom;
   a guidance along which said first and/or said second auxiliary centers can be moved, said guidance extending mirror-symmetrically with respect to a plane E that contains said axis A and that has a same second separation from each of said first and said second auxiliary centers, wherein said sample position can be moved relative to said guidance in an x-direction extending in said plane E, perpendicularly to said axis A.

2. The diffractometer of claim 1, wherein a separation between said source and said sample position is equal to a separation between said sample position and said detector.

3. The diffractometer of claim 1, wherein said guidance extends in a straight line.

4. The diffractometer of claim 1, wherein said first and said second auxiliary centers can be moved in opposite directions on said guidance.

5. The diffractometer of claim 1, wherein said first auxiliary center, said source and said sample position define a first triangle in said common plane M and said second auxiliary center, said detector and said sample position define a second triangle in said common plane M.

6. The diffractometer of claim 5, wherein said first triangle and said second triangle are equilateral triangles.

7. The diffractometer of claim 1, further comprising a motor drive for moving said sample position relative to said guidance.

8. The diffractometer of claim 7, wherein said guidance is stationary and said sample position can be moved along a stationary rail by means of said motor drive.

9. The diffractometer of claim 7, wherein said guidance comprises a threaded rod that is driven by said motor drive.

10. The diffractometer of claim 7, further comprising a control means for said motor drive, said control means advancing said sample position in said x-direction in accordance with a predetermined time function x(t).

11. The diffractometer of claim 10, wherein said detector sweeps a same angular increment within a same time.

12. The diffractometer of claim 10, wherein said control means advances said sample position in said x-direction in accordance with a predetermined time function x(t) with d/dt x(t)=const., and further comprising an evaluation means which takes into consideration a non-linear dependence Θ (x) for determining an intensity profile I(Θ) of the sample.

13. The diffractometer of claim 12, wherein said control means corrects an intensity $I(t_i)$ determined in a time interval $t_i$ through multiplication by a factor of $$\frac{d\vartheta}{dx}\bigg|_{x_i},$$

wherein i is an index of integral individual measurements and $x_i$ an average x-value for an individual measurement i.

14. The diffractometer of claim 1, wherein said detector is a one-dimensional detector with an elongated detector window, wherein said detector window lies in said common plane M over an entire length thereof.

15. The diffractometer of claim 1, wherein said diffractometer is designed in such a fashion that a sample disposed at said sample position maintains an orientation thereof during relative motion of said sample position with respect to said guidance.

16. The diffractometer of claim 15, wherein the sample is horizontal.

17. The diffractometer of claim 15, wherein the sample is vertical.

* * * * *